United States Patent
Fleischman et al.

(10) Patent No.: US 9,028,067 B1
(45) Date of Patent: May 12, 2015

(54) RELOCATED VIRTUAL RETINAL IMAGE METHOD AND SYSTEM

(71) Applicants: Jay Fleischman, Aspen, CO (US);
Jerald A Bovino, Greenwich, CT (US)

(72) Inventors: Jay Fleischman, Aspen, CO (US);
Jerald A Bovino, Greenwich, CT (US)

(73) Assignee: Sightex LLC, Greenwich, CT (US)

( * ) Notice: Subject to any disclaimer, the term of this patent is extended or adjusted under 35 U.S.C. 154(b) by 0 days.

(21) Appl. No.: 14/288,887

(22) Filed: May 28, 2014

(51) Int. Cl.
*A61B 3/14* (2006.01)
*G02C 5/00* (2006.01)
*A61B 3/113* (2006.01)
*G02C 7/02* (2006.01)

(52) U.S. Cl.
CPC ........... *G02C 5/001* (2013.01); *A61B 3/113* (2013.01); *G02C 7/02* (2013.01); *G02C 2202/10* (2013.01)

(58) Field of Classification Search
CPC ....................................................... A61B 3/113
USPC ................. 351/205, 206, 209, 211, 221
See application file for complete search history.

(56) References Cited

U.S. PATENT DOCUMENTS

| 5,067,019 A | 11/1991 | Juday et al. |
| RE45,062 E | 8/2014 | Maguire |
| 2014/0313484 A1* | 10/2014 | Bogaert ................. 351/211 |

OTHER PUBLICATIONS

Robert W. Massof, Douglas L. Rickman, Peter A. Lalle. Low Vision Enhancement System. Johns Hopkins APL Technical Digest, vol. 15, No. 2 (1994).
Robert W. Massof. Electro-Optical Head-Mounted Low Vision Enhancement. Practical Optometry 9:6 1998.

* cited by examiner

*Primary Examiner* — Mahidere Sahle
(74) *Attorney, Agent, or Firm* — Patent Law Office of Rick Martin, P.C.

(57) ABSTRACT

A diseased retina has a blind spot where the center of the retina, called the fovea, exists. A compensation system could comprise first measuring a patient's healthy regions of the retina called PRL. A video camera could be mounted on a table, such as for reading applications, but preferably mounted on an eyeglass frame, capture an area of regard (AR). This AR is sent to a computer which directs a projector (such as a MEMS projector) to direct the AR using his healthy area of his retina. Improvements include adding an eyeball location sensor to keep the AR focused on a moving PRL. Another improvement is dithering the AR image in millimeter sized oscillations on the moving PRL. Reading enhancement software such as Spritz® can be integrated into the computer to display the enhanced text onto the PRL.

19 Claims, 8 Drawing Sheets

RELOCATED VIRTUAL RETINAL IMAGE METHOD AND SYSTEM

FIELD OF INVENTION

The present invention relates to video capturing a desired image and displaying that image away from a diseased central area of the retina, the fovea, and onto a functioning area of the retina which contains an area called the preferred retinal locus (PRL).

BACKGROUND OF THE INVENTION

The center of the retina is anatomically identified as the macula, and in particular, the center of the macula, the area responsible for best vision, is known as the fovea. This specialized area of the retina must be disease free for optimal central vision to occur. Many different retinal diseases, for example Age Related Macular Degeneration (ARMD), can destroy the fovea and/or the surrounding macula area and thereby cause an area of blindness. This area of central blindness results in a black hole in the patient's vision known as a scotoma. Such patients will have their critical central vision severely compromised. ARMD, typically found in patients over 50 years of age, is reaching epidemic proportions. Its effects are often devastating both in terms of mobility and daily living functions. Attempts to improve levels of vision in patients with macula disease have mostly centered on methods that simply magnify the image (telescopic spectacle or handheld lenses, or simple video magnification systems), vary the image contrast or color, or attempt to displace the image with simple prisms. See U.S. Pat. No. 7,901,072 (2011) to Eagan et. al. These methods are overly simplistic and have proven to be mostly ineffective.

Retina specialists have heard from many patients and families of patients with poor central vision, "most of the time I can't see anything." However there are moments when they, surprisingly, see a small object, such as a needle on the floor only to be frustrated, a moment later, that the same object "disappears" from view. Since the macula and fovea are damaged in these patients, it is apparent that "eccentric viewing" must somehow account for these momentary improvements in visual function. Eccentric viewing in macular disease is well known to exist, whereby the patient momentarily uses a region of peripheral healthy retina. Unfortunately, only fleeting moments of vision are realized. Even with relatively small lesions, the disease-induced destruction of the fovea results in a scotoma that prevents effective fixation (necessary to keep the eyes locked in on an object) that would keep the area of regard (AR) in view for longer periods. Each time an ARMD patient attempts to return to "find" that small object, the central scotoma prevents them from being able to regain the AR and hold it in view. Only through random body positional and/or eye movements might the object be momentarily seen again. These random retakes of the image do not provide the patient with any practical degree of visual capability.

To overcome this impaired vision, some visually-impaired people have trained themselves to view objects at an angle, e. g., by looking at things out the corner of their eye. In this way, light is introduced through the pupil at a perceptible angle. In addition, many devices and procedures have been developed with the goal of alleviating the loss of sight resulting from macular degeneration and other vision impairments.

Prism correction has been added to prescription lenses of glasses for individuals with impaired vision to direct a viewed image to functioning or preferred portions of the retina. The required prism is determined by a subjective refraction using discrete steps of prism diopter and base, and once prescribed, the prism is built into the glasses. Because it is ground into the lens of the glasses, the prism cannot be changed without reexamination and the subsequent production of new spectacles. More significantly, the prism corrected image, because of its fixed nature cannot account for patient head or eye movements and, therefore, cannot be made to consistently have an image fall upon functioning and viable retina.

Other measures for ARMD vision correction include wearable telescopic spectacles or intraocular lens implants that incorporate miniature telescopes. Telescopic methods are not a best solution because they do not redirect the image to a functioning portion of the retina, but merely enlarge the image so that more area of the retina is used to see only small fractions of an image at a time. Patients are frustrated by having to piece together these small fragments to gain perception of an area of regard (AR). Wearable telescopic spectacles are often tried initially only to end up "in the drawer", unused. Intraocular telescopic implants are surgically invasive, oftentimes irreversible, cannot be modified or further optimized to adapt to a patient's needs. They have not gathered widespread use likely because of the same image limitations of wearable telescopes.

U.S. Pat. No. 7,901,072 provides a personal video display device. The video display device includes a wearable frame, a mount, a first prism, and a second prism. The wearable frame contains an image display displaying an image perceptible by the wearer. The mount is selectively attachable to the wearable frame. The first prism is contained in the mount and is disposed between the image display and the wearer's eye. The prism has a first surface facing the image display and a second surface angled relative to the first surface. The second prism is contained in the mount and is disposed between the first prism and the wearer's eye. The second prism has a first surface receiving the image emitted from the second surface of the first prism and a second surface angled relative to the first surface through which the image exits the second prism and is directed to the wearer's eye. The first prism and the second prism are moveable relative to each other to alter the angle at which the image exits. The second prism and is directed to the wearer's eye. Specifically, in this above cited embodiment, its design is optimized to present images to a healthy retina with normal central vision. The need exists to have an eyeglass like device that can improve vision in wearers that do not have a healthy central retina and which effectively directs images away from their scotoma to their best available portion of the remaining healthy retina.

The purpose of the present invention, the Relocated Image Virtual Retinal Display (RIVRD), is to incorporate a visual system aid whereby the AR, that portion of the central vision that could not be seen because of the scotoma, is intentionally directed away from the scotoma. The present invention is designed to persistently project or present a "relocated" image (RI) obtained by a small video camera that is capturing the AR, onto the healthiest and greatest vision potential region available on the retina. This area of remaining best vision potential, unique and different for each individual, includes a region known as the preferred retinal locus (PRL). The location of a particular patient's PRL and surrounding "best remaining vision potential" can be reproducibly discovered and mapped using microperimetry techniques (for example, via use of a scanning laser ophthalmoscope). The PRL, including nearby adjacent areas, discovered and mapped for each specific patient, will be the new discrete retinal area that will be used as the point of central fixation for relocated images (RI). That is, the AR will be transformed to an RI that will be seen via the determined PRL region which will provide improved vision to the patient. The RIVRD must be programmed for each patient, but repeat testing of hundreds of patients will likely identify a most likely PRL region for each geographic type of central scotoma (since most are centered at the fovea and mostly differ by overall diameter of involvement) thereby reducing or eliminating the need for custom design in every case.

SUMMARY OF THE INVENTION

The main aspect of the present invention is to utilize a miniature video camera mounted on an eyeglass frame to capture an area of regard (AR) then, using an onboard microprocessor, programmed to remap for a micro electro mechanical (MEMS) scanning projector or a digital light processor (DLP) projector, display that AR on a healthy region of the retina (called the preferred retinal locus PRL) in patients who have lost central vision secondary to disease.

Another aspect of the present invention is to map the patient's retina and record both the geometry of the central vision loss as well as identify the best PRL area remaining in order for the onboard microprocessor to relocate the new remapped image to project upon this "best" area.

Another aspect of the present invention is to track the position of the constantly moving eye, nominally using an infrared tracking system, and, in real time, keep the MEMS or DLP projector aimed at the moving target PRL area where the RI must remain focused. Furthermore, the MEMS or DLP projector will be programmed to dither the RI around the PRL (micro movements in all cardinal directions) in order to prevent perceptual image fading (a requirement for image optimization and based upon known physiology of retinal function).

Another aspect of the present invention is to provide an alternate embodiment to the MEMS or DLP by using a heads-up video display mounted directly in front of the patient's eyeball. Its image will also be appropriately relocated to the PRL area, adjusted real-time to account for eye movements via input from the eye tracker and dithered as described above.

Another aspect of the present invention is to mount the video camera on a reading stand so as to scan the text in a book or document. Then this text image is sent to a controller that projects the text at a desired speed via a projector onto the PRL. Thus, a wheelchair patient could relax next to a table with his favorite book and have his head mounted projector send the words onto his PRL.

Another aspect of the present invention is to enable an electronic book or text contained in a computer such as a tablet to be controlled to feed a word at a time to the head mounted projector.

Other aspects of this invention will appear from the following description and appended claims, reference being made to the accompanying drawings forming a part of this specification wherein like reference characters designate corresponding parts in the several views.

An optical framework for the present invention is found in Pub. No. US 2013/0044042 assigned to Google®, Inc. The '042 publication is incorporated in its entirety herein by reference. See especially FIGS. 1, 2, 3A, 3B, 4.

In order to fully understand the underlying principles for the RIVRD invention, it is critical to first understand FIG. 1, a prior art 3-D topographic map representation of retinal visual function/sensitivity, i.e. visibility or acuity. The normal retina detects images when light of a certain brightness and size is naturally focused, from that image, onto its surface. The detection sensitivity of the retina varies in a precise way along its geographic planar extent. This sensitivity can be precisely mapped by techniques known as visual field testing (or perimetry) whereby normal subjects are required to subjectively respond to whether or not they can see targets of varying intensity and size presented in multiple peripheral areas of the visual field, while they are required to maintain central gaze by staring at a tiny fixation target. The most sensitive part of the retina, capable of seeing both the smallest and dimmest objects is that point of fixation represented at the peak 10 and known as the fovea. Other points on the 3-D plotted "mountain" represent reduced brightness and size sensitivity. That is, areas on the retina, at any distance away from the fovea, only respond to progressively brighter and/or larger stimuli. The slope and cross sections of the mountain depict this change in sensitivity and visual acuity. Larger and brighter targets on the retina are required for detection as the distance from the fovea is increased. What this graph does not well depict is the importance of steady fixation, maintained by the healthy fovea, which is required to generate the contours of the mountain.

If the fovea is diseased and a scotoma results, the eyes can no longer maintain fixation. The normal topographic map is altered in a dramatic way—the "mountain" top is loped off as shown in FIG. 2 and labeled "diseased".

The essence of this invention is to artificially redirect and stabilize images, to land on that area of functional healthy retina which includes the PRL rather than the diseased area of lost central vision. These relocated images, will significantly increase the patient's ability to perceive images and thus increase their acuity level.

In summary, we describe methods and devices that will present a relocated image (RI) to the patient such that the area of regard AR falls precisely and consistently on the determined PRL area. The RIVRD will incorporate an eye tracker, an infrared transmitter/receiver servo loop, to account for small gaze eye movements. This servo loop will constantly adjust the RI in order to keep it centered on the PRL area. This stable image, with displaced central details, will restore a degree of significant functional vision to the patient, not possible by other means.

Methods and Devices:

Normally, we can see images that are present or presented at a variety of image planes. In distance order going from optical infinity to the retinal surface they are: 1) at 6 meters and beyond 2) from beyond the corneal surface to 6 meters 3) at the corneal surface 4) at the natural or intraocular lens and 5) at the retinal surface. Regions 1 through 3 are extraocular and 4 and 5 are intraocular image planes.

A small video camera (may be free standing in one series of embodiments or mounted on an eyeglass frame in another) produces a digital video image of the AR. This digital image can be processed to create a RI (an image with the AR relocated onto the PRL area) such that central image details will be seen by the patient when appropriately presented with the scanned processed and relocated image. Eye movements will be instantaneously monitored via a corneal or pupil tracker mounted in a spectacle frame and the RI continuously adjusted such that the AR is always seen by the PRL area.

Various combinations for the location of the video camera or the location of the projected image plane lead to various embodiments. The RI may be projected or appear on a video monitor at planes away from the patient (regions 1 and 2) or towards a patient (regions 3, 4 and 5).

SUMMARY

The present invention provides a novel system to improve functional vision in patients with macular degeneration or with central scotomata induced by other causes. The system presents to the patient a shifted, relocated, and constantly adjusted retinal image to the undamaged region of retina with best visual potential, the preferred retail locus (PRL). The steps are:

1. Employ a scanning laser ophthalmoscope, for example, whereby microperimetry techniques will be used to uniquely identify both the scotoma and the PRL area in each patient for the purpose of programming the RIVRD to project a remapped image. This remapping of an image, and relocating it to avoid a non-functional area of the retina, is novel.
2. A method to receive an image through a video camera mounted on glasses (or alternative video input such as that obtained from a free-standing video camera) and present: 1) a remapped and constantly adjusted image, to account for small eye movements, on an external display (such as a glasses mounted display [ex: Google® glass '042 publication], computer monitor or projection screen) 2) a (micro electro mechanical system) MEMS or (digital light processor) DLP projected image directed to the retina or a special surgically implanted intraocular lens.
3. The use of a MEMS scanner (micro electro mechanical system) or a DLP (digital light projection) combined with an infrared LED emitter/receiver pair, to serve as a projector combined with an eye tracker. As the eye moves, the tracker will continuously and precisely provide eye positional data to readjust the MEMS or DLP image center of the remapped video image.
4. Since the MEMS or DLP can so rapidly respond (i.e. change the precise position of the RI, to even rapid saccadic eye movements (detected and modulated by the eye tracker) both are capable of projecting an overly stable image on the retina. These images are likely to fade because of known latency characteristics mediated by the retinal photoreceptors. In order to counteract this the MEMS or DLP will be preprogrammed to constantly make high speed and microscopic lateral movements known as dithering. These microscopic image movements of the RI, projected on the PRL area, is incorporated to prevent such perceptual image fading.
5. A controller input to the microprocessor that will allow the patient to vary the remapped image in many ways including magnification, horizontal/vertical elongation, and warping of the relocated retinal image to meet specific visual needs.

What is a MEMS or DLP projector?

MEMS are separate and distinct from the hypothetical vision of molecular nanotechnology or molecular electronics. MEMS are made up of components between 1 to 100 micrometers in size (i.e. 0.001 to 0.1 mm), and MEMS devices generally range in size form 20 micrometers (20 millionths of a meter) to a millimeter (i.e. 0.02 to 1.0 mm). They usually consist of a central unit that processes data (the microprocessor) and several components that interact with the surroundings such as microsensors. At these size scales, the standard constructs of classical physics are not always useful. Because of the large surface area to volume ratio of MEMS, surface effects such as electrostatics and wetting dominate over volume effects such as inertia or thermal mass.

The potential of very small machines was appreciated before the technology existed that could make them—see, for example, Richard Feynman's famous 1959 lecture There's Plenty of Room at the Bottom. MEMS became practical once they could be fabricated using modified semiconductor device fabrication technologies, normally used to make electronics. These include molding and plating, wet etching (KOH, TMAH) and dry etching (RIE and DRIE), electro discharge machining (EDM), and other technologies capable of manufacturing small devices. An early example of a MEMS device is the resonistor—and electromechanical monolithic resonator.

Micromirror devices are devices based on microscopically small mirrors. The mirrors are Microelectromechanical systems (MEMS), which means that their states and positions are controlled by applying a voltage between the two electrodes around the mirror arrays. In the case of DLP (invented by Texas Instruments), thousands of microscopic mirrors in a chip array controls tiny points of light, and together these individual pixels combine to form an entire digital image similar to those found in many modern video projectors or DLP projection televisions. Each entire video frame, with all horizontal and vertical pixels available at once, is usually updated at 60, 120 or 240 etc. times per second to produce a continuous projected video sequence. In a technology developed by Microvision, and described in this patent as a MEMS projector in contrast to a DLP projector, has a single mirror (on the order of 1.5 square millimeters), designed to move in two directions by voltages applied to perpendicularly attached galvanometer coils. In this device a video image is produced by rapidly "painting", by deflection of light beam(s) off the oscillating galvo-controlled mirror, individual horizontal raster lines from right to left, returning again to paint another horizontal line, and repeated enough times from top to bottom, until an entire single video frame is produced. The process is repeated for each frame (60 times per second for example) such that a continuous video sequence is produced. This process is analogous to older cathode ray technology wherein an electron beam painted the raster lines onto a phosphor coated glass. Either the MEMS galvo-mirror or DLP projector will be used to produce video images used effectively in the RIVRD.

Reading:

Reading is usually an extremely frustrating task for people with macular degeneration or other retinal conditions that produce central vision loss. The requirement to track a line of text in a linear fashion, usually from left to right, is frustrated by large portions of the text line, and the words within, to be missing. Magnification of the text may help to a certain extent by enlarging the image to a point where its size on the retina projects beyond the scotoma (blind area) but then reading becomes a task of trying to assemble only portions of each word or individual letters in one's mind until recognition is reached. Even if this minimal recognition can be achieved reading in this fashion is tedious, slow and a mostly ineffective process. Scrolling, pinching, and resizing a reading area doesn't fix the problem and especially frustrates people with central vision loss.

Furthermore, the task of looking at a static image, analyzing and understanding its content and meaning, is an extremely difficult task for someone with central vision loss, especially as the image complexity increases. For these individuals only small portions of the image can be perceived at a time since both horizontally and vertically scanned pieces of the image have to be mentally "assembled". This requirement is met with unreliable and varied success. Magnification alone does not fix this problem since more "pieces" have to be mentally assembled and that process proportionally increases the time required for recognition and image understanding, a goal that often is not accomplished.

Utilizing the RIVRD, blocks of text, lines of text, or individual words can be projected on to the PRL area. In addition, static images (ex: drawings, photos, schematics) can be broken down into smaller blocks of the original image. These deconstructed portions of the image can be adjusted to size by the user as well as presented at a user controlled rate. This method will restore significant reading and image comprehension capabilities to those with central vision loss.

In the case of a downloaded text or pdf file (from a computer, for example) the image will be input directly to the RIVRD microprocessor where image processing algorithms will be applied. The RIVRD will project image blocks, lines, or individual words, to the user's PRL. If we are using a video obtained/scanned page we would incorporate optical character recognition (OCR) to transform the video image into text characters. The OCR algorithm may be embedded into the RIVRD onboard computer or be uploaded to the cloud for processing and then downloaded as a text file for RIVRD presentation on the PRL.

A typical RIVRD user sequence is the user points either glass mounted or free-standing video camera at a page, presses keypad to create a "photo" of that page and the video photo image is decomposed or, in the case of text, OCR processed by the RIVRD onboard microprocessor (or "in the cloud") rendering that video image into digitized text. The user hears a beep that signals that RIVRD projection is starting and the remapped image portions are projected on to the user's PRL at a rate the user has chosen. Then the next image or page is done in similar fashion. If the image is already available as a text image (ex: Kindle, Web etc.) OCR preprocessing will not be required. The text will be directly processed by our algorithms and projected onto the PRL as described above.

The presentation of specially decomposed text and or images (as described above) utilizing our RIVRD technology, for patients with central vision loss from retinal disease, is a novel application.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE DRAWINGS

Figure 1:
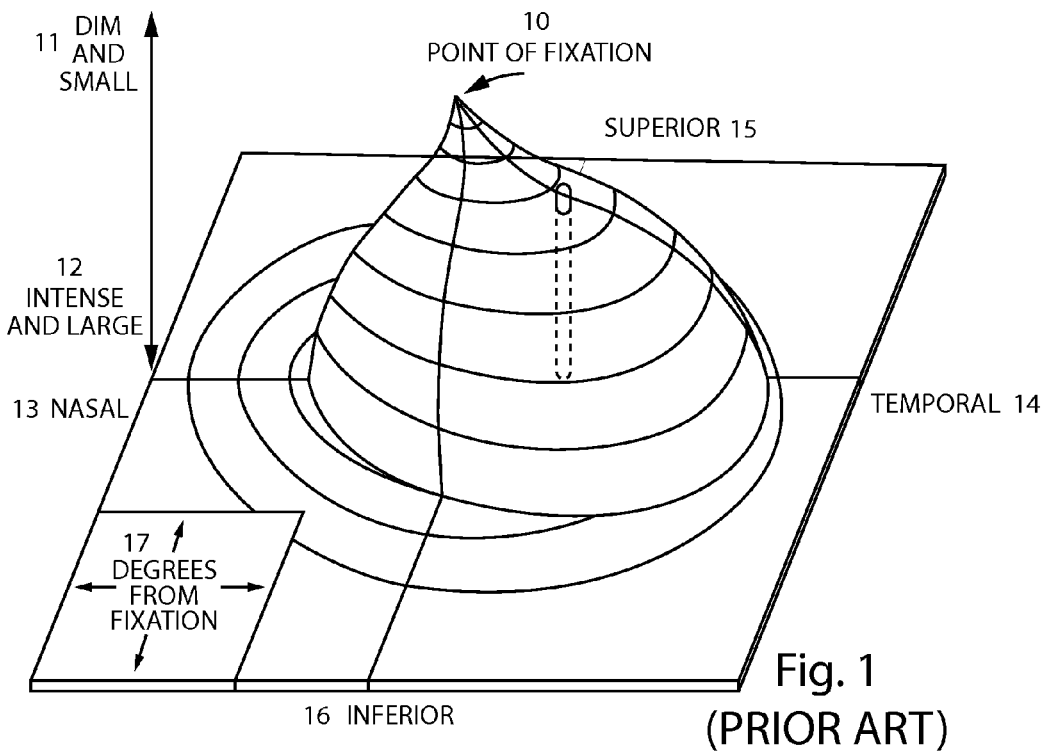
FIG. 1 (prior art) is a 3D model of a healthy retina.
Figure 2:
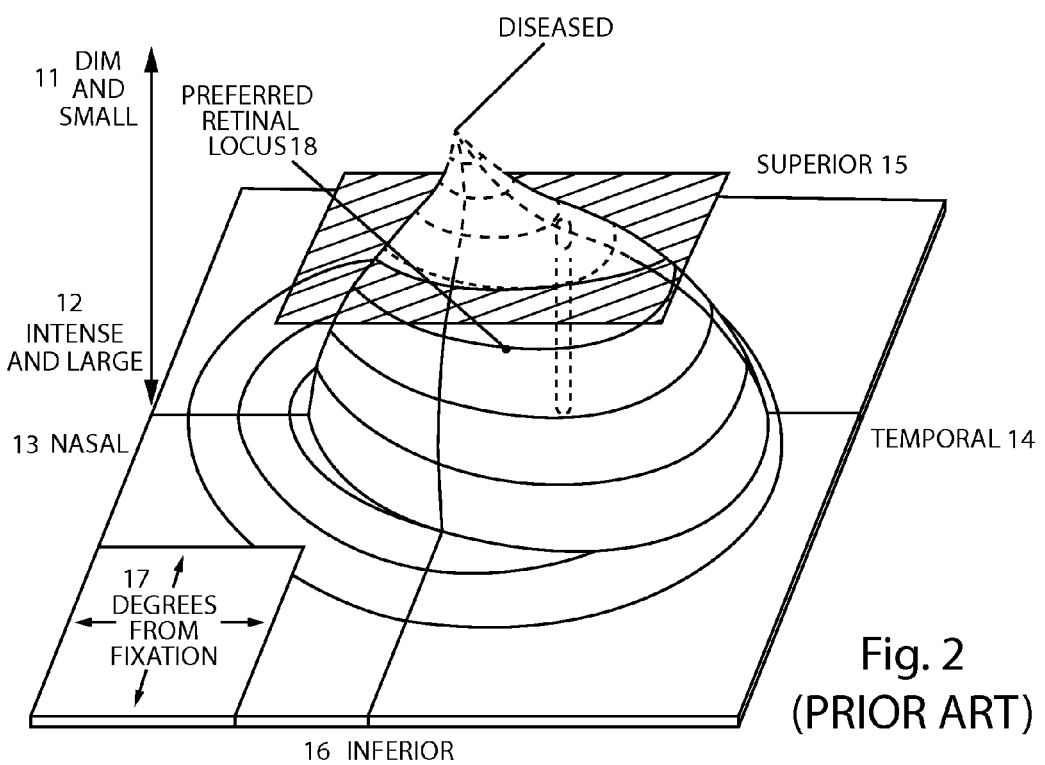
FIG. 2 (prior art) is a 3D model of a diseased retina.
Figure 3A:
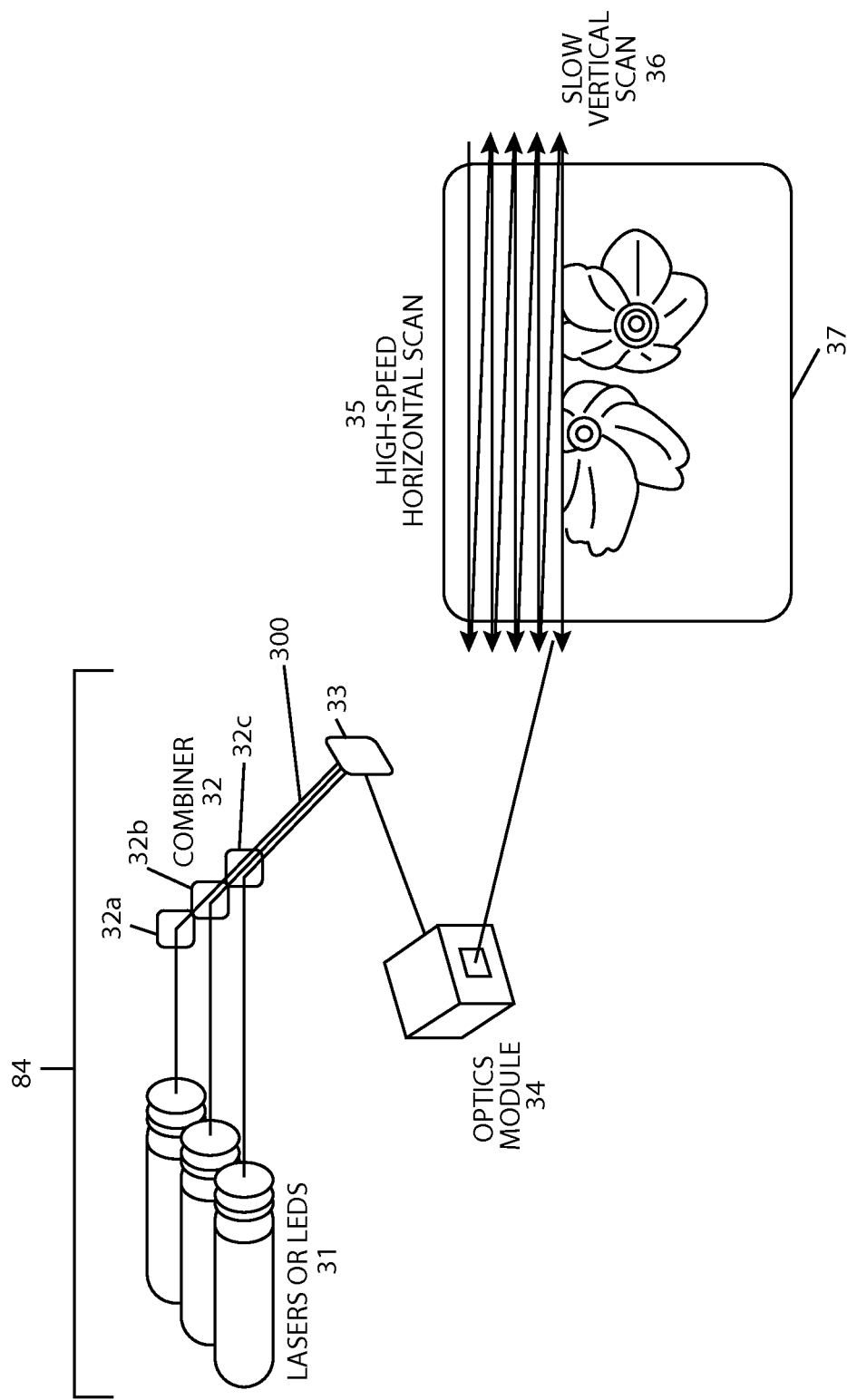
FIG. 3a (prior art) is a schematic view of a MEMS projector system.

Referring to FIG. 3a (prior art) the MEMS pico-projector module 84 of the present invention may be configured with three colored lasers or LED produced light sources 31 which would be red, green, blue. Combiner 32 consists of micro mirrors 32a, 32b, 32c that combine the three light beams and deflect a single beam 300 to a galvanometer controlled scanning mirror 33 then to optics module 34 which performs final image conditioning including magnification, focusing and dithering of the beam 300 to the pixel on screen, heads-up display, or retina 37 whereby the image will be seen by the PRL containing area by steering the laser beam in two dimensions—fast horizontal 35 and slow vertical 36. For scans directly "painted" on the retina the estimated retinal image size is about one square centimeter. For scans destined for either a heads-up display or screen in front and at a distance from the user, the image size can be varied by optics module 34.

Figure 3B:
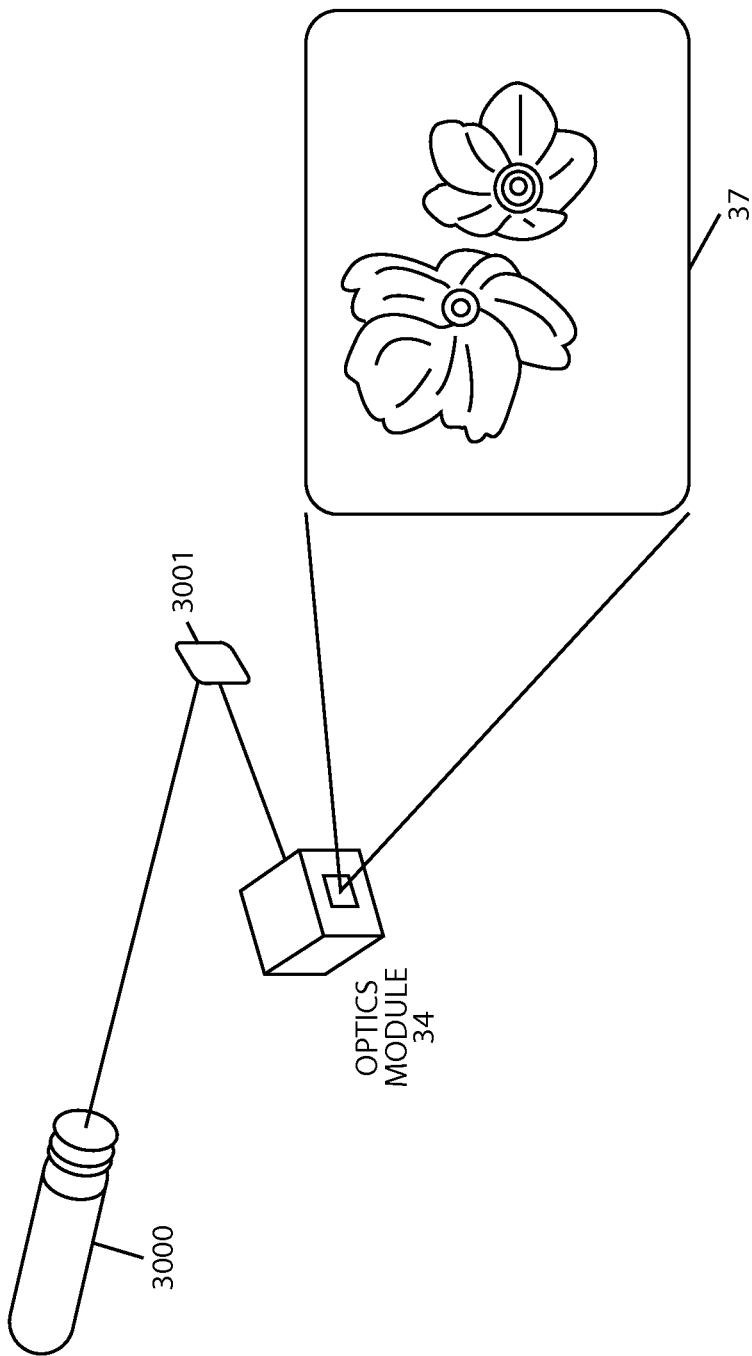
FIG. 3b (prior art) is a schematic view of a DLP projector.

Referring to FIG. 3b a digital light processor (DLP) implementation, and alternative to the galvanometer controlled single mirror MEMS projector, the 3 light sources 31 becomes a single white LED light source 3000. Combiners 32a-c are absent. Item 33 is now a DLP projector 3001 and 34 remains the final conditioning optics module. Items 35 and 36 no longer apply since the DLP generates an entire video frame at once as an array of colored pixels. These full frames are destined to be perceived by the user's PRL area in identical fashion as described for the galvanometer MEMs implementation.

Figure 4:
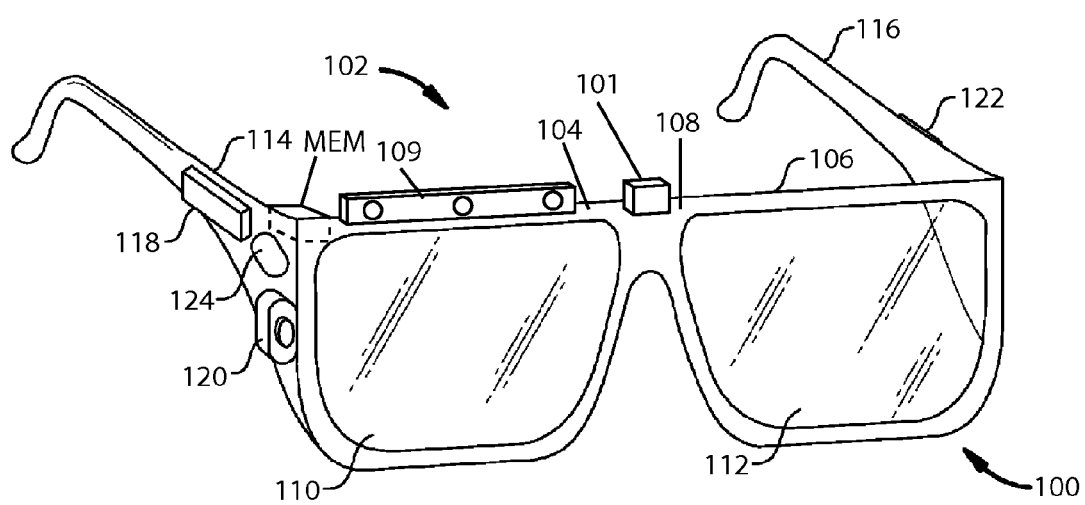
FIG. 4 is a front perspective view of an eyeglass frame mounted embodiment of the present invention.

Referring next to FIG. 4 an example system 100 is shown for receiving, transmitting, and displaying data. The system 100 is shown in the form of a wearable computing device. While FIG. 4 illustrates a head-mounted device 102 as an example of a wearable computing device, other types of wearable computing devices could additionally or alternatively be used. As illustrated in FIG. 4 the head-mounted device 102 comprises frame elements including lens-frames 104, 106 and a center frame support 108, lens elements 110, 112, and extending side-arms 114, 116. The center frame support 108 and the extending side-arms 114, 116 are configured to secure the head-mounted device 102 to a user's face via a user's nose and ears, respectively.

Each of the frame elements 104, 106, and 108 and the extending side-arms 114, 116 may be formed of a solid structure of plastic and/or metal, or may be formed of a hollow structure of similar material so as to allow wiring and component interconnects to be internally routed through the head-mounted device 102. Other materials may be possible as well.

One or more of each of the lens elements 110, 112 may be formed of any material that could optionally display a projected image or graphic. Each of the lens elements 110, 112 may also be sufficiently transparent to allow a user to see through the lens element. Combining these two features of the lens elements facilitate an reality or heads-up display where the projected image or graphic is superimposed over a real-world view as perceived by the user through the lens elements. This is a Google® (Pub. '402) eyeglass invention option that is designed to function for normal sighted individuals. Pub. '402's novel claims are designed such that a real-world view is not provided, but rather a computer generated virtual view. This function could be added to the present invention's function of project remapped and relocated images onto a retina to be perceived by a wearer with poor vision from a diseased central retina.

The extending side-arms 114, 116 may each be projections that extend away from the lens-frames 104, 106, respectively, and may be positioned behind a user's ears to secure the head-mounted device 102 to the user. The extending side-arms 114, 116 may further secure the head-mounted device 102 to the user by extending around a rear portion of the user's head. Additionally or alternatively, for example, the system 100 may connect to or be affixed within a head-mounted helmet structure. Other possibilities exist as well.

The system 100 must include an on-board computing system 118, a video camera 120, an optional sensor 112, and an optional finger-operable touch pad 124 which may be wired on the frame or wireless at another off-frame location). The on-board computing system 118 is shown to be positioned on the extending side-arm 114 of the head-mounted device 102; however, the on-board computing system 118 may be provided on other parts of the head-mounted device 102 or may be positioned remote from the head-mounted device 102 (e.g., the on-board computing system 118 could be wire- or wirelessly-connected to the head-mounted device 102). The on-board computing system 118 may include a processor and memory, for example. The on-board computing system 118 may be configured to receive and analyze data from the video camera 120 and the eye tracker 101, and generate images for output by the MEMS projector MEM to the PRL and optionally to the lens elements 110 and 112.

The video camera 120 is shown positioned on the extending side-arm 114 of the head-mounted device 102; however, the video camera 120 may be provided on other parts of the head-mounted device 102. The video camera 120 may be configured to capture images at various resolutions or at different frame rates. Many video cameras with a small form-factor, such as those used in cell phones or webcams, for example, may be incorporated into an example of the system 100.

Further, although FIG. 4 illustrates one video camera 120, more video cameras may be used, and each may be configured to capture the same view, or to capture different views.

The sensor 122 is shown on the extending side-arm 116 of the head-mounted device 102; however, the sensor 122 may be positioned on other parts of the head-mounted device 102. The sensor 122 may include one or more of a gyroscope or an accelerometer, for example. Other sensing devices may be included within or in addition to, the sensor 122 or other sensing functions may be performed by the sensor 122.

The finger-operable touch pad 124 is shown on the extending side-arm 114 of the head-mounted device 102. However, the finger-operable touch pad 124 may be positioned on other parts of the head-mounted device 102. Also, more than one finger-operable touch pad may be present on the head-mounted device 102. The finger-operable touch pad 124 may be used by a user to input commands such as adjusting the arm of the video camera 120. The finger-operable touch pad 124 may sense at least one of a position and a movement of a finger via capacitive sensing, resistance sensing, or a surface acoustic wave process, among other possibilities. The finger-operable touch pad 124 may be capable of sensing finger movement in a direction parallel or planar to the pad surface, in a direction normal to the pad surface, or both, and may also be capable of sensing a level or pressure applied to the pad surface. The finger-operable touch pad 124 may be formed of one or more translucent or transparent insulation layers and one or more translucent or transparent conducting layers. Edges or the finger-operable touch pad 124 may be formed to have a raised, indented, or roughened 20 surface, so as to provide tactile feedback to a user when the user's finger reaches the edge, or other area, of the finger-operable touch pad 124. If more than one finger-operable touch pad is present, each finger-operable touch pad may be operated independently, and may provide a different function. For low light or nighttime application an optional infrared LED illuminator 109 is shown.

The video camera 120 could be a daylight color camera or an infrared video camera (or combination of both) the latter requiring the infrared LED illuminator 109. The computing system 118 is generally meant to be preprogrammed with the patient's PRL area location, however, general preprogrammed probable and expected PRL area locations (by identifying the common features from other patient experiences) can be done.

Figure 9:
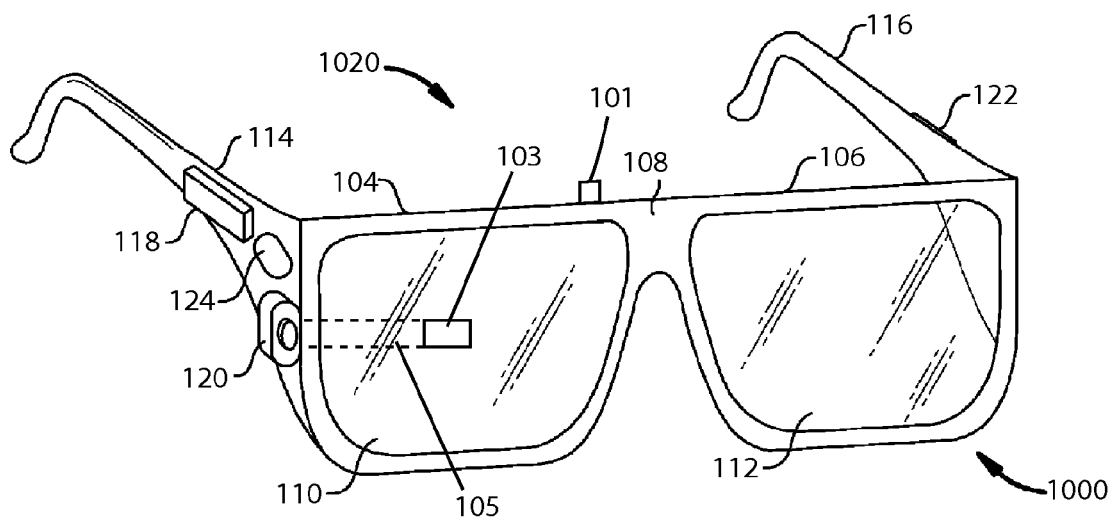
FIG. 9 is a front perspective view of an alternate eyeglass frame mounted embodiment.

In FIG. 9 shows embodiment 1000, a headpiece 1020. The MEMS projector MEM has been replaced with a heads-up display 103 fed by lines 105 attached to the computer 118. The relocated and dithered image is projected from the heads-up display 103.

Figure 5:
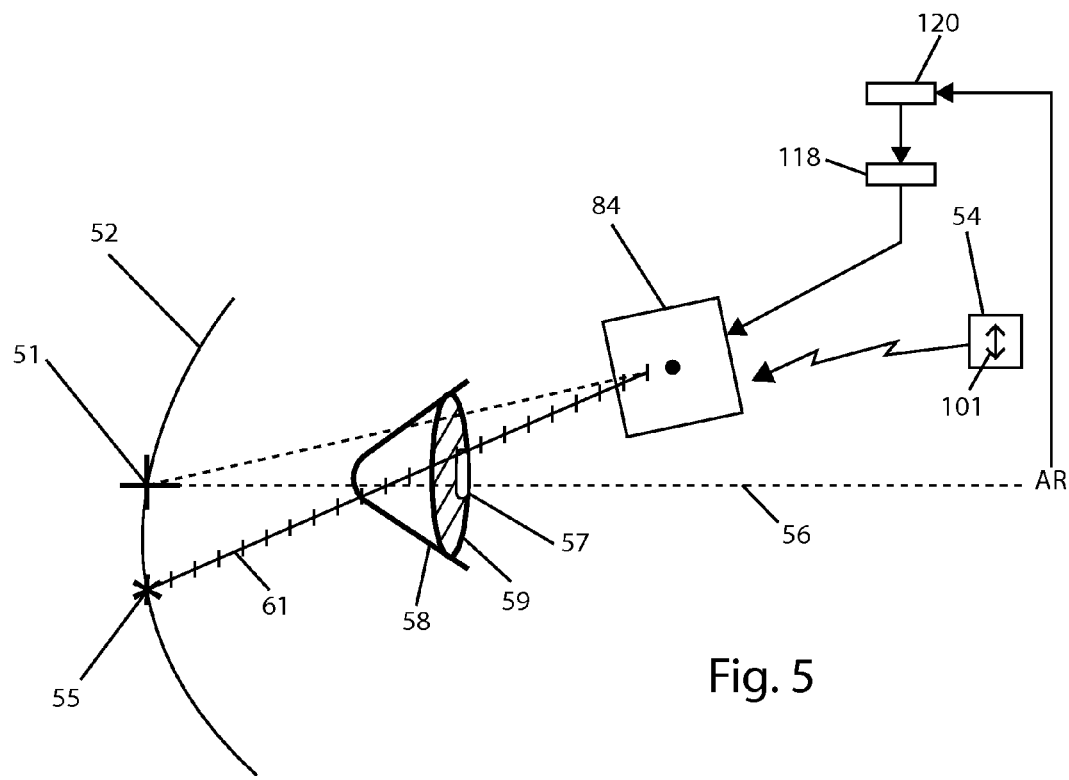
FIG. 5 is a schematic view of an area of regard (AR) being refocused to a healthy area of a retina called the preferred retinal locus (PRL).

Referring next to FIG. 5 the retina 52 has a diseased fovea at 51. The present invention identifies a healthy segment of the retina called the PRL at 55. The camera 120 has captured an area of regard AR and sent it to the computer 118 which projects, via the MEM or DLP projector 84 and path 61, the relocated image (RI) to the PRL area 55. Path 56 shows how a health eye 58 with iris 59 and pupil and natural lens 57 would normally focus the AR on the healthy fovea 51.

Figure 6:
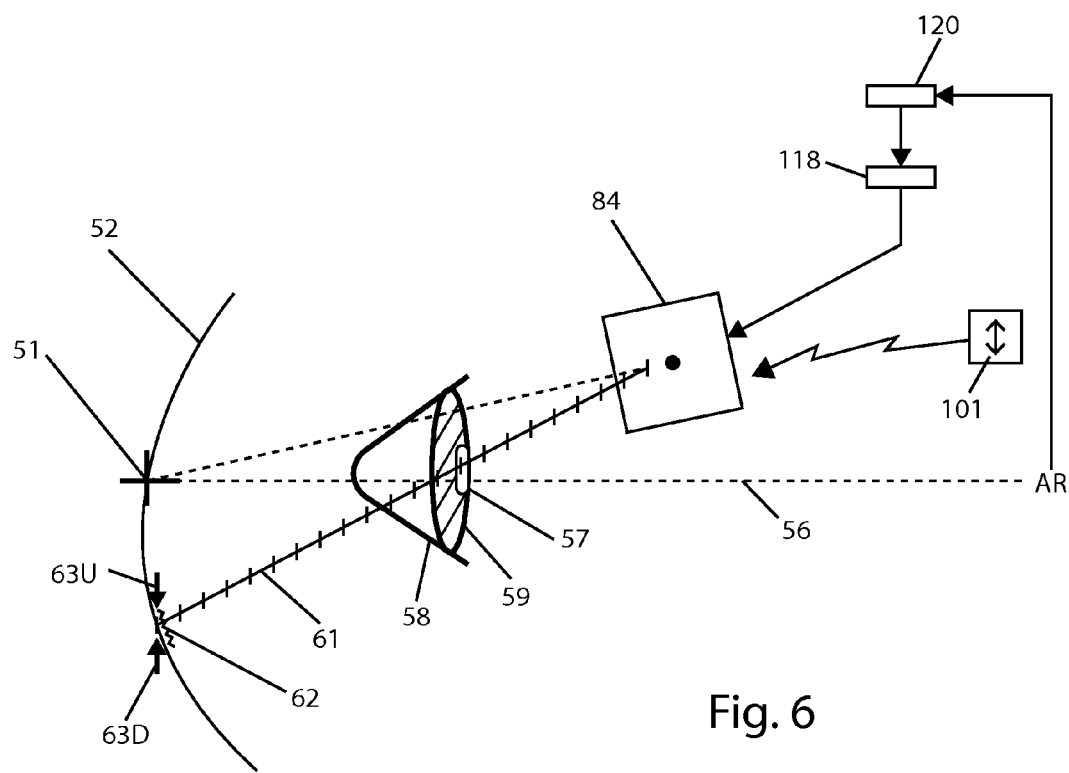
FIG. 6 is a schematic view of an eye tracker component of the system which moves the virtual AR in relation to the position of the eyeball.

Referring next to FIG. 6 the same system as shown in FIG. 5 is shown with two improvements. First the eye tracker 101 has been activated to move the MEM 84 and path 61 in synch with the eye 58 movements, as shown by new relocated images 63U and 63D. Second the RI is dithered, perhaps up, down and around and/or side to side as shown by jagged line 61. The eye tracker 101 functions by detecting reflected light off the corneal surface in a known manner. Deviations in the detected reflected beam are input to the microprocessor and instantaneous transformation calculations are used to synchronize the remapped image to keep it in stable position on the PRL area.

Figure 7:
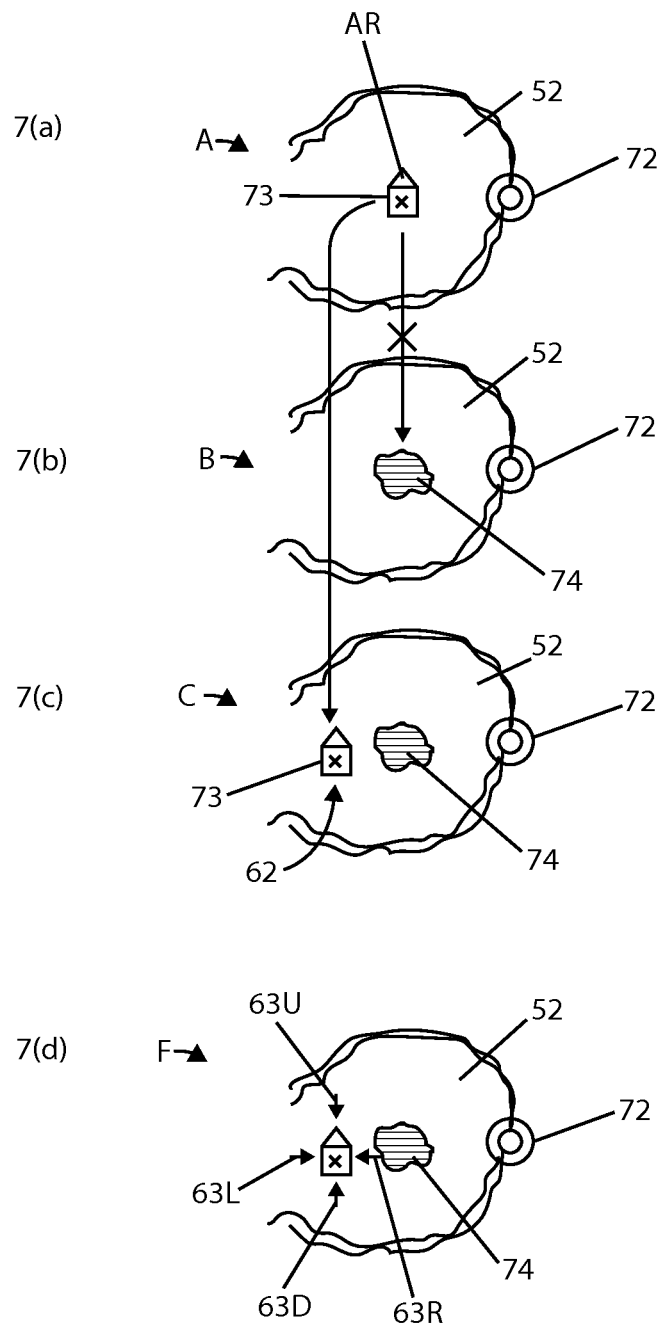
FIG. 7a is a depiction of an image on a healthy retina.
FIG. 7b is a depiction of a diseased retina.
FIG. 7c is a depiction of a relocated image on a diseased retina.
FIG. 7d is a depiction of the relocated image being moved in synch with the eyeball movement.

Referring next to FIGS. 7a-7d, FIG. 7a shows a healthy eye A with a retina 52, optic nerve 72, and the fovea 73 seeing the AR. In FIG. 7b the diseased eye 7b fovea 74 cannot see anything usually secondary to the depicted scar and resultant scotoma. In FIG. 7c using any of the embodiments of the present invention including those depicted in FIGS. 4 and 9, the AR 73 is relocated, and stabilized by data provided to the image microprocessor by eyetracker, at the PRL 62, and preferably dithered to prevent image fading. In FIG. 7d the AR is also moved in relation to the eye movement per FIG. 6 and dithered per 63U/D and 75L/R.

Figure 8:
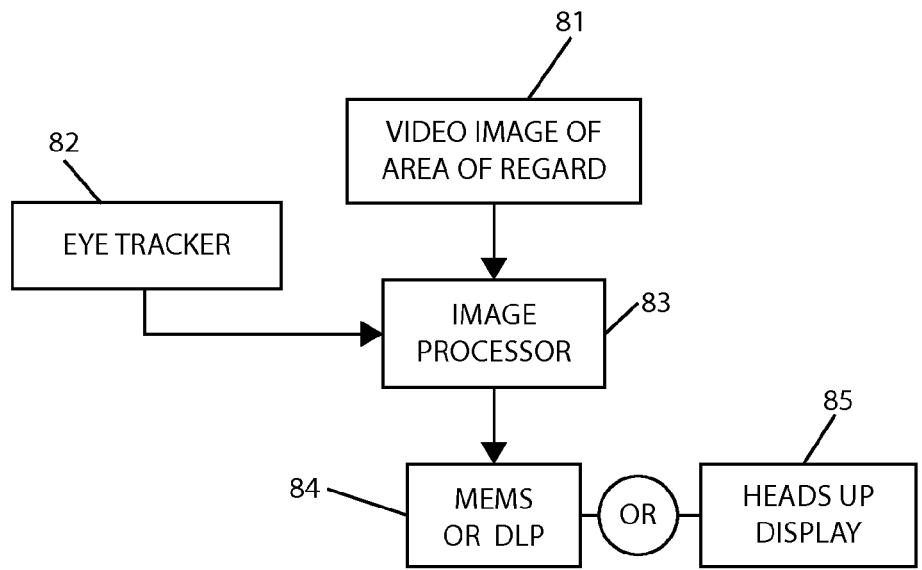
FIG. 8 is a flowchart of the inventive process.

Referring next to FIG. 8 a system overview is presented. A video device 81 captures an area of regard AR. This image of the AR is sent to computer 83 which also receives directional signals of eye movement from the eye tracker 82. The computer or image processor 83 directs the MEMS or DLP projector 84 or the heads up display 85 to the PRL area. The PRL ideally has been precisely preprogrammed into the computer 83 using precise eye measurements known in the art.

Figure 10:
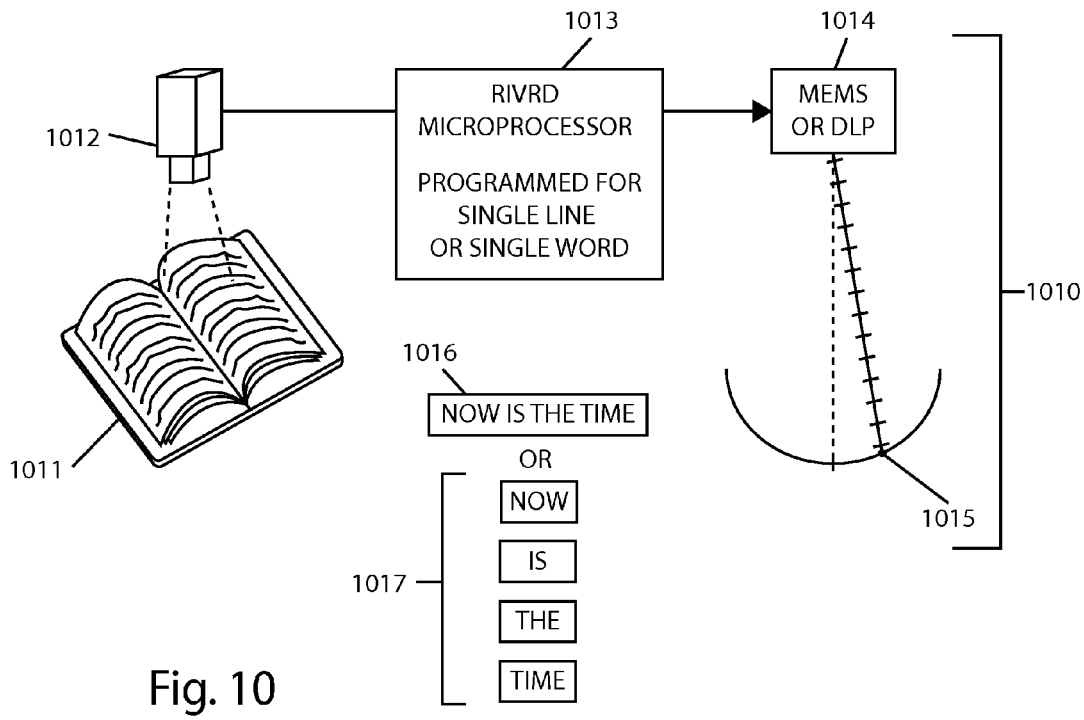
FIG. 10 is a diagrammatic view of a reading stand embodiment.

Referring next to FIG. 10 a reading system 1010 is comprised of a book (any written document) 1011 and a video camera 1012 which could be mounted on a stand (not shown). The microprocessor 1013 contains programming to capture left to right and line by line words of the text in book 1011. Drawings, photos and the like could be manually indicated by the reader using a keyboard stroke or equivalent, or the programming could have a module to distinguish words form drawings. The programming functions to isolate a single line or a single word or a drawing in sequence (for English) from left to right. Design choices for the programming include reading a page at a time and then isolating words and lines to send to the projector 1014. On just capturing one word at a time with the video camera 1012 then sending its digital code to the projector 1014.

The PRL 1015 could receive text, for example and not limiting the options, as a line 1016, or as a scrolling set of words 1017. The programming can be tuned for maximum contrast, ideal size, color, and rates of display. A reader's keypad (not shown) could offer real time adjustments to these and other variables. Enhanced reading software such as Spritz® described below could be included in the programming.

As an introduction to how and why Spritz® works let's start off with a few basics about reading.

Traditional reading involves publishing text in lines and moving your eyes sequentially from word to word. For each word, the eye seeks a certain point within the word, which is called the "Optimal Recognition Point" or ORP. After your eyes find the ORP, your brain starts to process the meaning of the word that you're viewing. With each new word, your eyes move, called a "saccade", and then your eyes seek out the ORP for that word. Once the ORP is found, processing the word for meaning and context occurs and your eyes move to the next word. When your eyes encounter punctuation within and between sentences, your brain is prompted to assemble all of the words that you have read and processes them into a coherent thought.

When reading, only around 20% of your time is spent processing content. The remaining 80% is spent physically moving your eyes from word to word and scanning for the next ORP. With Spritz® the software helps you get all that time back. For more in-depth scientific explanations about how Spritz® works, check out (http://www.spritzinc.com/blog/).

There are lots of other reading techniques out there such as skimming (not reading every word), avoiding sub-vocalization (talking to yourself while reading) and enlarging the peripheral span (reading an entire page at a time by mental "snapshot") that attempt to increase reading speeds. While these methods can be effective, achieving significant improvement requires intensive, continuous training and dedication. By contrast, Spritzing can be learned in less than 5 minutes and, if you don't Spritz for a month, no practice is needed to return quickly to your previous speed or skill-level.

In addition, none of these methods mentioned above help you unless you've got a lot of physical space for your content. From the fonts used to the algorithms that process content, Spritz is designed from the ground up to empower effective reading on a small display area.

Spritzing presents reading content with the ORP located at the specific place where you're already looking, allowing you to read without having to move your eyes. With this approach, reading becomes more efficient because Spritzing increases the time your brain spends processing content without having to waste tie searching roe the next word's ORP. Spritzing also enhances reading on small screens. Because the human eye can focus on about 13 characters at a time. Spritzing requires only 13 characters' worth of space inside the redicle. No other reading method is designed to help you read all of your content when you're away from a large screen.

Removing eye movement associated with traditional reading methods not only reduces the number of times your eyes move, but also decreases the number of times your eyes pass over words for your brain to understand them. This makes Spritzing extremeley efficient, precise, convenient and comfortable.

The Spritz engine is lightweight and uses patent-pending technologies to process and display content. The Spritz engine requires few system resources to process inbound content streams, making it easy for contain publishers and developers to integrate spritzing into their solutions. And since most of the work performed in the engine is text processing, extremely high spritzing speeds can be achieved, even on legacy devices and systems.

Reading is usually an extremely frustrating task for people with macular degeneration or other retinal conditions that produce central vision loss. The requirement to track a line of text in a linear fashion, usually from left to right, is frustrated by large portions of the text line, and the words within, to be missing. Magnification of the text may help to a certain extent by enlarging the image to a point where its size on the retina projects beyond the scotoma (blind area) but then reading becomes a task of trying to assemble only portions of each word or individual letters in one's mind until recognition is reached. Even if this minimal recognition can be achieved reading in this fashion is tedious, slow and a mostly ineffective process. Scrolling, pinching, and resizing a reading area doesn't fix the problem and especially frustrates people with central vision loss.

Utilizing the RIVRD, whereby lines of text can be projected to the PRL area, linear reading of text lines or individual words presented in rapid fashion (ref: Spritz®, WO2014011884, incorporated herein by reference) will restore significant reading capability.

Spritz® (as noted above) has developed an application that is a compact text streaming process, designed for normal sighted people, whereby content can be streamed one word at a time, without forcing eyes to spend time moving around the page. Spritz makes streaming content easy and more comfortable, especially on small displays. Their "Redicle" technology enhances readability even more by using horizontal lines and hash marks to direct the users eyes to the red letter in each word, so they can focus on the content that interests them. Furthermore, Spritz's technology can integrate photos, maps, videos, and website data to promote more effective readability. We will incorporate Spritz's algorithm in the RIVRD.

In the case of a downloaded text or pdf file (from a computer, for example) the image will be input directly to the RIVRD microprocessor where the Spritz algorithm will be applied to the image. The RIVRD will project lines, or individual words, of text to the user's PRL. If we are using a video obtained/scanned page we would incorporate optical character recognition (OCR) to transform the video image into text characters. The OCR algorithm may be embedded into the RIVRD onboard computer or be uploaded to the cloud for processing and then downloaded as a text file for RIVRD presentation on the PRL.

A typical RIVRD user sequence is the user points either glass mounted or free-standing video camera at a page, presses keypad to create a "photo" of that page and the video image is either OCR processed by the RIVRD onboard microprocessor (or "in the cloud") rendering that video image into digitized text. The user hears a beep that signals that Spritz is starting and lines or individual words are projected onto the user's PRL at a rate the user has chosen. Then the next page is done in similar fashion. If the image is already available as a text image (ex: Kindle, Web etc.) OCR preprocessing will not be required. The text will be directly processed by the Spritz algorithm and projected onto the PRL as described above.

Figure 11:
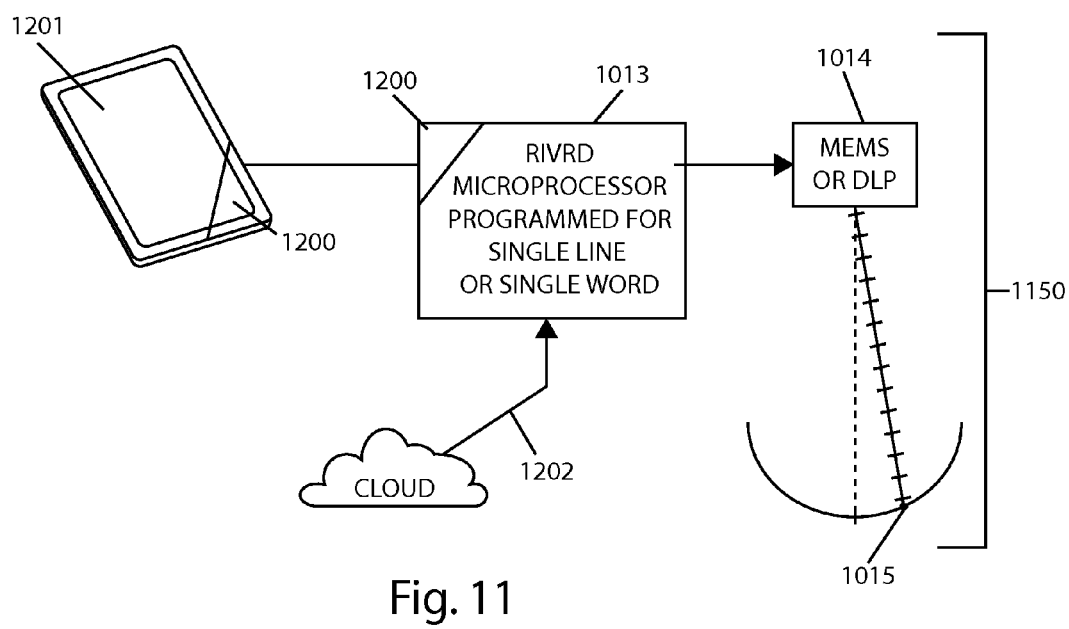
FIG. 11 is a diagrammatic view of an electronic book embodiment.

Referring next to FIG. 11 an electronic book 1200 is received by the system 1150 microprocessor 1013 either via a tablet 1201 or online 1202, or an equivalent. The programming in the microprocessor 1013 would manipulate the digital text to obtain the same results as embodiment 1010 in FIG. 10.

Although the present invention has been described with reference to the disclosed embodiments, numerous modifications and variations can be made and still the result will come within the scope of the invention. No limitation with respect to the specific embodiments disclosed herein is intended or should be inferred. Each apparatus embodiment described herein has numerous equivalents.

We claim:

1. A method to improve vision for a human with a diseased retina, the method comprising the steps of:
   determining that a central retina area called the fovea is damaged;
   determining an area around the damaged fovea (a preferred retinal locus PRL) which can function to transmit an image to the human's brain;
   storing the PRL retinal coordinates in an electronic memory;
   mounting a video camera to receive a desired image from an area of regard (the AR image);
   transmitting the AR image to a controller which has the retinal coordinate of the stored PRL;
   directing a projector to persistently project an unaltered AR image in its entirety to the PRL area, thus forming a relocated image (RI) on the PRL;
   mounting on an eyeglass frame the video camera, the controller and the projector; and
   mounting an eye tracker on the eyeglass frame and sending an eye position to the controller so the controller instantaneously changes the position of the RI image to keep it centered on the moving PRL.

2. The method of claim 1, further comprising the step of controlling the relocated image (RI) to a size of about one square centimeter.

3. The method of claim 1, further comprising the step of dithering the RI image on image on the PRL area to prevent image fading.

4. The method of claim 1, further comprising the step of using a MEMS or DLP device as the projector.

5. The method of claim 1, further comprising the step of using a heads-up projector as the projector.

6. An electronic device comprising:
   a frame configured to be worn on the head of a human, the frame including a bridge configured to be supported on the nose of the human, a brow portion coupled to and extending away from the bridge to a first end remote therefrom and configured to be positioned over a first side of a brow of the human, and a first arm having a first end coupled to the first end of the brow portion and extending to a free end, the first arm being configured to be positioned over a first temple of the human with the free end disposed near a first ear of the human;
   a battery power source connected to the frame;
   a video camera mounted on the frame;
   wherein an area of regard (AR) is viewed and captured by the video camera, and the AR is sent to a controller;
   a projector mounted on the frame;
   said projector image and direction being controlled by the controller;
   wherein the AR, is transformed by the controller remapped image (RI), and is projected by the projector to an alternate retinal area distinct from a diseased central fovea;
   wherein the frame further comprises an eye tracker which sends an eye position to the controller, wherein the projector is controlled to maintain the AR on the moving alternate retinal area; and
   wherein a pre-mapped alternate retinal area called the preferred retinal locus (PRL) is stored in the controller, and the projector is directed to the PRL by the controller.

7. The electronic device of claim 6, wherein the controller directs the projector to dither the AR on the PRL.

8. The electronic device of claim 6, wherein the projector further comprises a HEHS projector.

9. The electronic device of claim 6, wherein the projector further comprises a heads-up projector.

10. A method to improve the vision of a human with a diseased retina, the method comprising the steps of:
    determining the human has a diseased fovea;
    determining an alternate area of the retina that can function better than the diseased fovea;
    capturing an area of regard (AR) with a camera to form an AR image;
    projecting the IR image onto the alternate area using a projector;
    wherein the determining step comprises predefining a shaped area around the diseased fovea based in part on the human's age and eyeball size and storing this predefined shaped area of the retina in a memory of a controller that controls the projector;
    mounting the camera and the projector on a head frame; and
    mounting an eye tracker on the head frame and forwarding an eye position to the controller so as to maintain the RI image on the moving PRL.

11. The method of claim 10, wherein the determining step further comprises optically measuring and mapping the alternate area (PRL) and storing the coordinates of the PRL in a memory of a controller that controls the projector.

12. The method of claim 10 further comprising the step on having the controller dither the RI image on the PRL.

13. The method of claim 1, further comprising the step of measuring and mapping the area around the damaged fovea for determining the PRL.

14. The method of claim 1, further comprising the step of estimating the PRL using a plurality of historical measurements of a plurality of patients.

15. The method of claim 1, further comprising the step of using an infrared tracking system as the eye tracker.

16. The method of claim 1, further comprising the step of surgically implanting an intraocular lens to receive the projected AR image, the surgically implanted intraocular lens focusing the AR image to the PRL.

17. The method of claim 1, further comprising the step of using the controller to magnify the AR image before projecting the AR image.

18. The method of claim 1, further comprising the step of providing a user input device to input commands to the controller.

19. The method of claim 18, further comprising the step of using a finger-operable touch pad mounted on the eyeglass frame as the user input device.

* * * * *